United States Patent [19]

Orth et al.

[11] Patent Number: 4,785,110
[45] Date of Patent: Nov. 15, 1988

[54] PROCESS FOR THE PRODUCTION OF 2-AMINO-3-NITRO-6-(4-FLUOROBENZYLAMINO)-PYRIDINE

[75] Inventors: Winfried Orth, Hassloch; Jürgen Engel, Alzenau; Peter Emig, Niederdorfelden; Gerhard Scheffler, Hanau; Hans Pohle, Bielefeld, all of Fed. Rep. of Germany

[73] Assignee: Degussa Aktiengesellschaft, Frankfurt am Main, Fed. Rep. of Germany

[21] Appl. No.: 843,253

[22] Filed: Mar. 24, 1986

[30] Foreign Application Priority Data

Mar. 23, 1985 [DE] Fed. Rep. of Germany ....... 3510623

[51] Int. Cl.$^4$ ................................................ C07D 213/75
[52] U.S. Cl. ..................................... 546/307; 546/308
[58] Field of Search ................................. 546/308, 307

[56] References Cited

U.S. PATENT DOCUMENTS 3,481,943 12/1969 Thiele et al. .................... 546/308
4,481,205 11/1984 Von Bebenburg ............... 546/308

FOREIGN PATENT DOCUMENTS 1695637 8/1972 Fed. Rep. of Germany ...... 546/307

Primary Examiner—Mary C. Lee
Assistant Examiner—Zinna Northington
Attorney, Agent, or Firm—Cushman, Darby & Cushman

[57] ABSTRACT

There is described a process for the production of 2-amino-3-nitro-6-(4-fluorobenzylamino)-pyridine which consists essentially of reacting 2-amino-3-nitro-6-methoxypyridine with 4-fluorobenzylamine in water at elevated temperature; in a given case the nitro group can be subsequently reduced and a carbethoxy group introduced.

7 Claims, No Drawings

PROCESS FOR THE PRODUCTION OF 2-AMINO-3-NITRO-6-(4-FLUOROBENZYLAMINO)-PYRIDINE

BACKGROUND OF THE INVENTION

From German patent No. 1695637 there is known the process of exchanging an alkoxy group in the 6-position of a 3-nitro-pyridine for a substituted amino group. However, this reaction cannot be carried out without modification if there is additionally present an amino group in the 2- position of the pyridine compound which is to be reacted.

SUMMARY OF THE INVENTION

It has now been unexpectedly found that in the reaction of 2-amino-3-nitro-6-methoxypyridine with 4-fluorobenzylamine in water as the reaction medium there is exclusively carried out an exchange of the methoxy group in the 6-position for the 4-fluoro-benzylamine, that is the desired end product is obtained in a 96% yield. In contrast the yields in other solvents, such as for exmaple alcohols, dioxane, toluene, or mixture of these agents with water are considerably lower, whereby at the same time there is also carried out an exchange of the amino group in the 2-position and there are obtained difficultly separable mixtures, in which there are also always found considerable amounts of unreacted starting pyridine compound.

The 2-amino-3-nitro-6-(4-fluoro-benzylamino)-pyridine is an important intermediate product for the production of the analgetically active medicine 2-amino-3-carbethoxyamino-6-(4-fluoro-benzylamino)-pyridine and presents a second and new improved way for the production of this active material. The previous production is carried out by nitration of the 2,6-dichloropyridine, reaction of the thus obtained 2,6-dichloro-3-nitropyridine with ammonia with exchange of the chlorine atom in the 2-position for the amino group and subsequent reaction with 4-fluoro-benzylamine, whereby the chlorine atom in the 6-position is then replaced by the 4-fluoro-benzylamino radical. There is then obtained in this manner 2-amino-3-nitro-6-(4-fluoro-benzylamino)-pyridine. The 2,6-dichloro-3-nitropyridine used in this method of production, however, has the great disadvantage that it is a very reactive material, which causes allergies; furthermore, the production of this material (nitration of 2,6-dichloro-pyridine) is dangerous since the reaction sometimes proceeds explosively.

Therefore, the method of synthesis proposed in the invention signifies a considerable simplification, greater safety and improved environmental conditions in the production of 2-amino-3-carbethoxy-amino-6-(4-fluoro-benzylamino)pyridine.

The process of the invention involving the reaction with 4-fluoro-benzyl amine is carried out for example in water at a temperature between 70° and 150° C., preferably between 90° and 120° C. In a given case with temperatures above 100° C. operation is carried out in an autoclave.

There is used for 1 mole of 2-amino-3-nitro-6-methoxy-pyridine for example 1 to 4 moles, preferably 2 moles, of 4-fluoro-benzylamine. The 4-fluoro-benzylamine can also be employed as a salt. Especially there can be used the salts of 4-fluoro-benzylamine with inorganic acids respectively mineral acids (for example the hydrochloride, hydrosulfate, sulfate or hydrobromide).

In this case it is necessary that before or during the heating the aqueous reaction mixture be heated with the stoichiometrically necessary amount of basic material (suitably as an aqueous solution) in order to set free the 4-fluoro-benzylamine base. As basic materials there can be used for example alkali hydroxides (NaOH, KOH), alkali carbonates ($K_2CO_3$, $Na_2CO_3$), tertiary amines, preferably lower aliphatic amines (triethylamine). In the event that the 4-fluoro-benzylamine is employed in the form of a salt there can also be used for example the following procedures:

A solution of 2-moles of the 4-fluoro-benzylamine salt in 200–900 ml of water, preferably in 400 ml of water, is neutralized with 2 moles of a basic material in for example 100–200 ml of water and this mixture then is added to a suspension of 1 mole of the pyridine-exchange components in 1—1.7 liters of water, preferably 1.5 liters of water, with stirring and the thus obtained mixture is heated.

The reaction time, depending on the reaction temperature, is between 5 and 15 hours. For example, the reaction time at 75° C. is 14 hours, at 120° C. in an autoclave 7.5 hours.

Per 1 mole of 2-amino-3-nitro-6-methoxy-pyridine there is used for example 1 to 3.5 liters, preferably 1.5 to 2.5 liters of water.

Suitably the reaction mixture after the end of the reaction is subjected to a steam distillation at normal pressure or under reduced pressure (200 mbar to 20 mbar), whereby unreacted 4-fluoro-benzylamine distills off and is recovered from the aqueous distillate by extraction with diethyl ether and can be used again as starting materials.

It has proven especially suitable for the reduction of the nitro group to use catalytic hydrogenation. As catalysts for example there can be used:

Raney-nickel, nobel metals such as palladium and platinum as well as compounds thereof, with and without carriers, such as for example barium sulfate, calcium sulfate, etc. It is recommended to carry out the hydrogenation of the nitro group at a temperature between 20 and 100° C. and a pressure of approximately 1 to 70 bar in a solvent. As solvents there are suited for example $C_1$-$C_4$-alkanols, e.g. methyl alcohol, ethyl alcohol, propyl alcohol, isopropyl alcohol, butyl alcohol, cyclic ethers such as dioxane and tetrahydrofuran, ethoxyethanol, water, aromatic hydrocarbons (benzene, toluene, xylene) as well as mixtures of these agents.

It is advantageous in many cases for the subsequent isolation of the reduced compounds if there is added at the beginning to the mixture to be hydrogenated drying agents such as water-free sodium or magnesium sulfate.

However, the reduction can also be carried out with nascent hydrogen, for example zinc/hydrochloric acid, tin/hydrochloric acid, iron/hydrochloric acid or with salts of hydrogen sulfide in alcohol/water at about 70° to about 120° C. or with activated aluminum in water containing ether at 20° to 40° C. with tin(II)-chloride/hydrochloric acid.

The thus obtained reaction product is suitably to reacted immediately in the resulting reaction mixture with a compound which is suited to replace a hydrogen atom of amino group in the 3-position obtained by the reduction by the carbethoxy group —CO—$OC_2H_5$, without needing to isolate the 2,3-diamino-6- benzylamino-pyridine derivative. This is especially true in the case of catalytic hydrogenation. It goes without saying that this last mentioned compound can also be isolated and then the carbethoxy group introduced. The introduction can be carriedout in the customary manner with the customary reagents for this. Examples of such reagents are: ethyl haloformates such as ethyl chloroformate, bromoformate or iodoformate. Since the free starting amine (2,3-diamino-pyridine-derivative) is sensitive to oxygen, operation is suitably carried out under a nitrogen atmosphere.

The introduction of the carbethoxy group is generally carried out in an inert solvent or suspension agent at a temperature between 0° and 60° C., especially 5° to 40° C., preferably 20° to 25° C. As solvents there can be used: saturated alicylic and cyclic ethers (dioxane, tetrahydrofuran, lower dialkyl ethers such as diethyl ether, diisopropyl ether), lower alkanols such as ethanol, isopropanol, butanol, lower aliphatic ketones (acetone, methyl ethyl ketone), lower aliphatic hydrocarbons or halohydrocarbons (methylene chloride, chloroform, 1,2-dichloroethane), aromatic hydrocarbons (benzene, toluene, xylene), lower dialkylamides of lower saturated aliphatic carboxylic acids (dimethylformamide, dimethylacetamide), tetramethyl urea, N-methyl-pyrrolidone, dimethyl sulfoxide or mixtures of those agents.

In general the reactants are reacted in equimolar amounts. However, in a given case it can be suitable to employ a reactant in slight excess. In a given case the reaction also can be carried out in the presence of basic or acid binding agents such as alkali carbonates (potassium carbonate, sodium carbonate), alkali bicarbonates, e.g. sodium bicarbonate or potassium bicarbonate, alkali acetates,e.g. sodium acetate or potassium acetate, alkali hydroxides, e.g. sodium hydroxide or potassium hydroxide or tertiary amines (for example triethylamine).

The latter is especially true if haloformic acid esters are employed.

Depending on the process conditions and starting materials the product of the process is obtained in the free form or in the form of its salt. This salt can in turn be converted in known manner, for example with alkali or ion exchangers, into the free base. From the latter by rection with organic or inorganic acids there can in turn be obtained the salts. As such acids there can be mentioned for example hydrohalic acids, e.g. hydrochloric acid, hydrobromic acid, hydroiodic acid, sulfuric acid, phsophoric acid, phosphorous acid, nitric acid, perchloric acid, organic mono-, di-, or tricarboxylic acids of the aliphatic, alicyclic, aromatic or heterocyclic series as well as sulfonic acids. Examples of these acids are: formic acid, acetic acid, propionic acid, succinic acid, glycolic acid, lactic acid, malic acid, tartaric acid, citric acid, ascorbic acid, maleic acid, furmaric acid, hydroxymaleic acid or pyruvic acid, phenylacetic acid, benzoic acid, p-aminobenzoic acid, anthranilic acid, p-hydroxybenzoic acid, salicylic acid or p-aminosalicylic acid, embonic acid, methanesulfonic acid, ethanesulfonic acid, hydroxyethanesulfonic acid, ethylenesulfonic acid, halobenzenesulfonic acids, e.g. chlorobenzenesulfonic acid, toluenesulfonic acid, naphthalenesulfonic acid or sulfanilic acid.

The process can comprise, consist essentially of, or consist of the states steps with the recited materials.

DETAILED DESCRIPTION

Example

A mixture of 33.8 grams (0.2 mole) of 2-amino-3-nitro-6-methoxy-pyridine and 50.1 grams (0.4 mole) of 4-fluoro-benzylamine in 400 ml of water were heated to boiling for 10 hours with a reflux condenser, then with increasing cooling in the course of 3 hours a mixture of water and 4-fluoro-benzylamine distilled off. (The distillate was extracted with ether, dried and the ether distilled in a vacuum, Residue of 4-fluoro-benzylamine: 19 grams.) The suspension remaining behind was cooled, the resultant crystalline compound removed by suction filtering, purified with water and dried in a vacuum.

Yield: 49.9 grams (95.2% of theory).
Melting Point: 172°–176° C. (with decomposition).

Example for the Reduction of Nitro Group and Introduction of the Carbethoxy Group 2-amino-3-carbethoxyamino-6-(4-fluoro-benzylamino)-pyridine

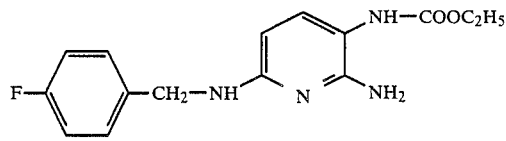

26.2 grams (0.1 mole of 2-amino-3-nitro-6-(4-fluoro-benzylamine)-pyridine were hydrogenated with 15 grams of Raney-nickel in 250 ml of dioxane at 50° C. and 30 atmospheres absolute. The solution was rendered free of catalyst by filtering with suction. The solution freed of catalyst by suction filtering was treated with stirring with 10.8 ml (0.13 mole) of ethyl chloroformate, whereby the hydrochloride crystallized out after 15 minutes. These crystals were filtered with suction and recrystallized from water.

M.P. of the hydrochloride 214°–215° C.

The entire disclosure of German priority application No. P 3510623.9 is hereby incorporated by reference.

What is claimed is:

1. A process for the production of 2-amino-3-nitro-6-(4-fluoro-benzylamino)-pyridine wherein the materials employed consist essentially of: (a) 2-amino-3-nitro-6-methoxy-pyridine; (b) 4-fluoro-benzylamino; and (c) water at an elevated temperature.

2. A process according to claim 1 wherein the temperature is 70° to 150° C.

3. A process according to claim 2 wherein the temperature is 90° to 120° C.

4. A process according to claim 3 wherein there are used 2 moles of 4-fluoro-benzylamine per mole of the 2-amino-3-nitro-6-methoxy-pyridine.

5. A process according to claim 1 wherein the materials employed consist essentially of: (a) 2-amino-3-nitro-6-methoxy-pyridine; (b) 4-fluoro-benzylamine or a salt thereof; and (c) water.

6. A process according to claim 4 wherein the materials employed consist essentially of: (a) 2-amino-3-nitro-6-methoxy-pyridine; (b) 4-fluoro-benzylamine or a salt thereof; and (c) water.

7. A process according to claim 4 wherein the materials employed consist essentially of: (a) 2-amino-3-nitro-6-methoxy-pyridine; (b) 4-fluoro-benzylamine; and (c) water.

* * * * *